United States Patent [19]

Brunck et al.

[11] Patent Number: 5,714,580
[45] Date of Patent: Feb. 3, 1998

[54] TRYPSIN INHIBITORS

[75] Inventors: Terence K. Brunck; Michael G. Pepe, both of San Diego; Daniel A. Pearson, Solana Beach; Thomas R. Webb, Encinitas, all of Calif.

[73] Assignee: Corvas International, Inc., San Diego, Calif.

[21] Appl. No.: 455,974

[22] Filed: May 31, 1995

Related U.S. Application Data

[63] Continuation of Ser. No. 11,666, Jan. 29, 1993, Pat. No. 5,534,498, which is a continuation-in-part of Ser. No. 828,388, Jan. 30, 1992, abandoned.

[51] Int. Cl.$^6$ ............... C07K 5/00; C07K 7/00; C07K 17/00

[52] U.S. Cl. ............... 530/331; 530/333; 530/332; 530/335; 530/337; 564/34; 564/36

[58] Field of Search ............... 530/331, 333–335, 530/337; 564/34, 36

Primary Examiner—Toni R. Scheiner
Assistant Examiner—Sheela J. Huff
Attorney, Agent, or Firm—Lyon & Lyon LLP

[57] ABSTRACT

Novel compounds having activity against trypsin are disclosed. Specifically, novel peptide aldehyde analogues that have substantial potency and specificity as inhibitors of mammalian pancreatic trypsin are presented. The compounds are useful in the prevention and treatment of the tissue damage or destruction associated with pancreatitis.

6 Claims, 3 Drawing Sheets

TRYPSIN INHIBITORS

RELATED APPLICATIONS

This is a continuation of U.S. patent application Ser. No 08/011,666, filed Jan. 29, 1993, now U.S. Pat. No. 5,534, 498, issued Jul. 9, 1996, which is a continuation-in-part of U.S. patent application Ser. No. 07/828,388, Jan. 30, 1992 now abandoned and hereby incorporated by reference herein, including the drawings attached thereto.

FIELD OF THE INVENTION

This invention relates to inhibitors of trypsin useful for treatment of pancreatitis.

BACKGROUND OF THE INVENTION

In a healthy mammal, the pancreas produces and secretes enzymes that digest carbohydrates, fats and proteins in the gastrointestinal tract. They are produced in inactive form (termed proenzyme) and subsequently are converted to an active form in the small intestine giving rise to a cascade of amylolytic, lipolytic and proteolytic activity. The cascade is thought to begin with the conversion of pancreatic trypsinogen to trypsin catalyzed by enterokinase, a proteolytic enzyme associated with the small intestine. The newly-formed trypsin then converts the other pancreatic proenzymes into their active forms to trigger a burst of enzymatic activity characterized as digestion. Greenberger et al., Diseases of the Pancreas, "Harrison's Principles of Internal Medicine," 11th Edition, p. 1372, McGraw-Hill, (E. Brunewald et al. edit, 1987).

In the absence of perturbing factors, the pancreas is able to protect itself from the autodigestion which could result from the digestive enzymes it produces. The pancreatic acinar cells (where the digestive enzymes are synthesized and stored) provide three control mechanisms to prevent their own destruction. First, the enzymes are produced as catalytically inactive proenzymes. Second, after their synthesis, but before secretion into the digestive system, the enzymes are segregated from the acinar cell cytoplasm in lysosomes (membrane-bound intracellular organalles). Third, the lysosomes containing the enzymes contain potent protein inhibitors of trypsin which prevent premature activation of other hydrolytic proenzymes. Steer el al., New England Journal of Medicine, 316: 144 (1987).

In the presence of perturbing factors, a disorder of the pancreas termed pancreatitis (either acute or chronic) may result. Acute pancreatitis can manifest itself as a mild and self-limiting disorder (termed edematous pancreatitis), or in a more severe form (termed necrotizing pancreatitis) where permanent damage to pancreatic tissue occurs. Chronic pancreatitis results in extensive and permanent destruction of the pancreas. Greenberger et al., supra, at 1372.

Acute pancreatitis is usually associated with biliary tract stones, while chronic pancreatitis is often associated with chronic alcohol abuse. Steer et al., supra, at 144. Pancreatitis may also arise as a complication of cardiac surgery involving cardiopulmonary bypass procedures, and is reported to follow all types of open-heart surgery, including cardiac transplantation. Castillo et al., New England Journal of Medicine, 325: 382 (1991). Moreover, bouts of acute pancreatitis are occasionally induced following gastrointestinal diagnostic and surgical procedures, such as bile duct exploration, sphincteroplasty, distal gastrectomy, splenctomy, and endoscopic retrograde cholangiopancreatography. Bardenheier et al., Am. J. Surg. 116: 773 (1968); Cotton. Gut, 18: 316 (1977). Significant pancreatic injury has been reported in 1 to 3% of patients suffering from abdominal trauma which occasionally results in obstructive chronic pancreatitis.

Pancreatitis is characterized by damage to the pancreas and surrounding tissues which arises from autodigestion of the cells by the various digestive enzymes activated by trypsin. Animal studies of chemically-induced pancreatitis suggest that the disorder is rooted in the inability of pancreatic acinar cells to excrete the digestive proenzymes. This results in the activation of trypsinogen to trypsin by lyosomal hydrolases within the cell, with the amount produced exceeding protective levels of protease inhibitor normally available. Steer et al., supra, at 148; Gabryelewicz, Digestion, 40: 19 (1988). This results in the subsequent activation of the other digestive enzymes co-localized with trypsin in the lysosome. These activated digestive enzymes cause edema, interstitial hemorrhage, vascular damage, coagulation necrosis, fat necrosis and parenchymal cell necrosis, Greenberger et al., supra, at 1372.

The activated digestive enzymes may subsequently enter the blood and the peritoneal cavity and can lead to secondary multiple organ damage. Although the blood contains trypsin inhibitors, it has been reported that trypsin complexed with one such inhibitor, alpha-2-macroglobulin, remains active. Rinderknecht et al., Biochim. Biophys. Acta. 295: 233 (1973); Harpel et al., J. Clin. Invest., 52: 2175 (1975); Rinderknect et al., Biochim. Biophys. Acta, 377: 158 (1975). This active complex is thought to contribute in part to the metastatic proteolytic damage observed in pancreatitis. Jones, et al., Gut, 23: 939 (1982).

A number of compounds have been examined for treatment of pancreatitis. Specifically, aprotinin, Futhan, Foy, Foy-305 and the leupeptins.

Aprotinin is a polypeptide of 58 amino acids and is reported to be a potent inhibitor of trypsin, with a dissociation constant ($K_d$) of $3 \times 10^{-11}$M. Jones, supra, at p. 939. However, it is also reported to be ineffective in the treatment of human acute pancreatitis. Imrie et al., Br. J. Surg., 65: 337 (1978); M.C.R. Working Party, Lancet ii: 632 (1977); Niederau et al., supra, at 1061. Aprotinin is also an inhibitor of the coagulation factors, kallikrein and plasmin with a $K_d$ of $1 \times 10^{-7}$M and $2 \times 10^{-10}$M respectively. Kassell et al., Biochem. Biophys. Res. Commun., 18: 225 (1965); Fritz el al., Arzneim. Forsch. 33: 479 (1983); Lazdunski et al., *Protein-ase Inhibitors*, p 420, Springer Verlag (H. Fritz et al. ed. 1974); Trautschold et al., Biochem. Pharmacol., 16: 59 (1967).

Futhan is a nonpeptidyl low molecular weight protease inhibitor first synthesized by Fuji et al., Biochim. Biophys. Acta, 661: 342 (1981). It is also known as nafamstat mesilate, FUT-175, and 6-amidino-2-naphthyl-4-guanidino benzoate dimethanesulfonate. It is reported to be effective in the treatment of acute pancreatitis induced in animal models. Iwaki et al., Jap. J. Pharmac. 41: 155 (1986); Gabryelwicz et al., supra, at p 22. It is a potent inhibitor of trypsin, as well as the coagulation enzymes, kallikrein, factor Xa, and thrombin. Aoyama et al., Japan J. Pharmacol., 35: 203 at 209 (1984); Hitomi et al., Hemostasis, 15: 164 (1985).

Foy (also known as gabexate mesilate) and Foy-305 (also known as camostate) are also nonpeptidyl low molecular weight protease inhibitors. Both are reported to be effective to varying degrees in the treatment of acute pancreatitis induced in animal models. Niederau et. al., J. Clin. Invent. 78: 1056–1063, 1986. Lankisch et al., Gastroenterology, 96: 193 (1989). Both compounds are reported to be effective inhibitors of trypsin, as well as the coagulation/fibrinolysis enzymes, kallikrein, thrombin, plasmin and C1r complement system enzyme. Muramutu et al., Biochim. Biophys. Acta, 268: 221 (1972); Takasugi et al., J. Med. Sci., 29: 188 (1980); Tamura et al., Biochim. Biophys. Acta, 484: 417 (1977).

The leupeptins are low molecular weight peptidyl aldehydes consisting of N-acetyl-L-leucyl-L-leucyl-L-argininal, N-propionyl-L-leucyl-L-leucyl-L-argininal and their analogs which contain L-isoleucine or n-valine in place of L-leucine. Aoyagi et al., "Structures and Activities of Protease Inhibitors of Microbial Origin", Proteases and Biological Control, pp. 429–454, Cold Spring Harbor Laboratory. Press (Reich et al. edit. 1975). They are reported to prolong the survival of rats in which acute pancreatitis has been induced. Jones, supra, at p. 939. They are potent inhibitors of trypsin and other serine proteases. Chi et al., J. Antibiotics, XLII: 1506 (1989).

Various derivatives of the leupeptins have been disclosed which are also potent inhibitors of trypsin. N-benzyloxycarbonyl-L-pyroglutamyl-L-leucyl-L-argininal was shown to be a potent inhibitor of trypsin (with an $IC_{50}$ about 7 times lower than than that for N-acetyl-L-leucyl-L-leucyl-L-argininal) (Saino et al., J. Antibiotics, XL1: 220 (1988)).

U.K. Patent Application 2,153,825 and Japanese Application 60-163815 describe naphthalene derivatives of arginine as trypsin inhibitors useful for treatment of pancreatitis; and Niederau et al., Gastroenterology 88: 1192 (1985) describe proglumide, benzotript and secretin as protective agents against caerulein-induced pancreatitis in mice.

Abbreviations

The following abbreviations are used in this application.

"Bn" refers to benzyl.

"Boc" refers to t-butoxycarbonyl.

"BOP" refers to benzotriazol-1-yloxy-tris-(dimethylamino)-phosphonium-hexafluorophosphate.

"CDI" refers to carbonyldiimidazole.

"DCM" refers to dichloromethane.

"DIEA" refers to diisopropylethylamine.

"DMF" refers to N,N-dimethylformamide.

"Fm" refers to 9-fluorenemethyl.

"IPA" refers to isopropanol.

"MeOH" refers to methanol.

"NaOAc" refers to sodium acetate.

"NMM" refers to 4-methylmorpholine.

"Ph" refers to phenyl group.

"Ppa" refers to protected peptide or analog.

"TBS" refers to 0.1M Tris, 0.14M sodium chloride, pH 7.4.

"TEA" refers to triethylamine.

"TFA" refers to trifluoroacetic acid.

"THF" refers to tetrahydrofuran.

SUMMARY OF THE INVENTION

Applicants have discovered that compounds having the general structure:

where Pr is a hydrophobic group; $A_1$ is glutamic acid (Glu) or aspartic acid (Asp), or an equivalent of Glu or Asp; $A_2$ is proline (Pro) or an equivalent of Pro having a 4- or 5-membered ring structure; $A_3$ is Argininal (Arg-aldehyde or Arg-al) or an equivalent thereof are very specific and active trypsin inhibitors. In contrast to previously described trypsin inhibitors these compounds show potency and selectivity. That is, the described compounds have little to no inhibitory activity [i.e., have an $IC_{50}$ value substantially greater (i.e., more than ten fold greater) than that with trypsin] against one or more other serine proteases with physiologically significant activities, including those involved in blood clotting, e.g., kallikrein, thrombin and the activated coagulation factors XII, XI, IX, VII, X, and II; serine proteases involved in clot dissolution e.g., plasmin, tissue plasminogen activator (tPA), and urokinase (UK); serine proteases involved in clot prevention e.g., Protein C; and serine proteases involved in complement mediated cell lysis, e.g., C1r and C1s. See, Colman et al., "Overview of Hemostasis" at pp 3–15, Bachmann, "Plasminogen activators", at pp 318–339, Owen, "Protein C", at 235–241 in Hemostasis and Thrombosis, Basic Principles and Clinical Practice, 2nd Edition, J.B. Lippincott Company (Colman et al. edit., 1987), and Eisen, "Complement", Microbiology, 3rd Edition, p. 456, Harper & Row (Davis et al., 1980). Because of their unexpected selectivity, these compounds will be advantageous over other trypsin inhibitors known in the art because they will not have undesirable side effects resulting from inhibiting other useful and necessary protease activities in the body. This property also permits the compounds to be administered intravenously and orally with few side effects.

By "equivalent" is meant to include variations in the general structure of one or more amino acids or hydrophobic groups which have little if any deleterious affect on the inhibitory activity of the compound compared to the use of the designated amino acid or hydrophobic group. Such variations are well known in the art and can be determined without undue experimentation. They include those variations in the general formula shown below. For example, the hydrophobic group is hydrophobic enough to provide a potent inhibitory activity. Arginine equivalents will function to direct the inhibitor to the active site of trypsin. Examples of such equivalents include an L-or D-isomer of argininal, homoargininal, guanidinoaminobutyral, guanidinoaminopropional, $(Me_2)Arg$, $(Et_2)Arg$, p-aminomethyl-phenylalaninal, p-amidinophenylalanine, p-guanidinophenyl-alanine, a conformationally constrained arginine analog as described by T. R. Webb and C. Eigenbrot, J. Org. Chem. 56: 3009 (1991), or mono- or di-substituted N-alkyl derivative thereof wherein alkyl means a lower alkyl, preferably methyl. The Glu or Asp is a carboxylated non-cyclic amino acid and equivalents thereof. Such equivalents would include γ-R' esters of glutamic acid, β-R' esters of aspartic acid, or R'-substituted tetrazoles where the tetrazole substituted for the carboxylic acid group of Glu or Asp. R' in these equivalents is H, lower alkyl of 1 to 6 carbons, or aralkyl of about 6 to about 15 carbon atoms; and the Pro is a cyclic (preferably 4 or 5 membered ring) compound, not including a hydroxy group in the ring, examples include D- or L- isomers of proline, β-methylproline, ββ-dimethylproline; dehydroproline, azetidine carboxylic acid.

This invention also provides a pharmaceutical composition for the prevention and treatment of pancreatitis, which includes one of the above compounds formulated as a pharmaceutically acceptable salt combined with a pharmaceutically acceptable carrier. The invention also provides a method for prevention of, or treatment of, pancreatitis.

Thus, in various aspects, the invention features novel peptide aldehydes, their pharmaceutically acceptable salts, and therapeutic compositions comprising these pharmaceutically acceptable salts in a suitable pharmaceutical diluent for use in the prevention and treatment of pancreatitis, or other diseases characterized by an elevated level of trypsin activity. The novel compounds include those having the general formula:

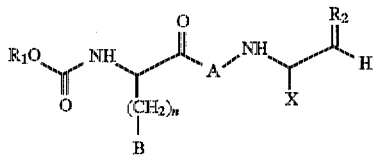

where $R_1$ is a branched alkyl, a cyclic or polycyclic alkyl (which may be substituted with one or more alkyl groups, preferably of 1 to 5 carbon atoms) of 4 to 10 carbons, n is 1, 2 or 3; A is a group having the formula:

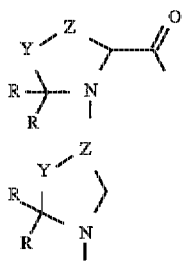

where Y, and Z are independently selected from a direct link, oxygen atom and methylene group where only one of Y and Z can be a direct link or an oxygen atom and each R is independently H or an alkyl group with 1 or 2 carbon atoms; B is selected from a group consisting of —$CO_2H$, —$CO_2R'$,

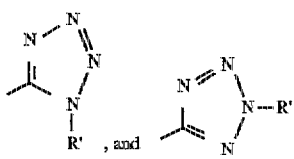

is —$(CH_2)_3$—NH—C(=NH)—$NH_2$, —$(CH_2)_3$—C(=NH)—$NH_2$, 4-amidinophenylmethyl, 4-guanidinylphenylmethyl, or 4-aminomethylphenylmethyl, and their mono- and di-substituted N-alkyl derivatives, wherein the alkyl group is methyl, ethyl, propyl, isopropyl, butyl or isobutyl; and $R_2$ is oxygen or N—$NR_3$—C(=O)—$NR_4$, where $R_3$ is hydrogen, an alkyl group of 1 to 6 carbons, a phenyl group, an aralkyl group of 7 to 9 carbons, and $R_4$ is hydrogen, an alkyl group of 1 to 6 carbons, a phenyl group, an aralkyl group of 7 to 9 carbons, or a peptide or peptide analog, provided that N—$NR_3$—C(=O)—$NHR_4$ is readily hydrolyzed at low pH to give the derivative with an oxygen atom. By such peptide analog derivatives having $R_2$ as N—$NR_3$—C(=O)—$NHR_4$ is meant to include pro-drug forms of inhibitors of this invention which can be orally administered, and which in the low pH (e.g., 6.0 or less) of the stomach are cleaved to produce a potent trypsin inhibitor of the invention.

It is known that peptidyl arginine aldehydes exist in equilibrium structures in aqueous solutions. See, Bajusz, S., et al., J. Med. Chem., 33: 1729 (1990). These structures, as shown below, include the arginine aldehyde, A, aldehyde hydrate, B, and two amino cytol forms, C and D. The R group would represent the remainder of a given compound embodied in the present invention. The peptide aldehydes of the present invention include within their definition all their equilibrium forms.

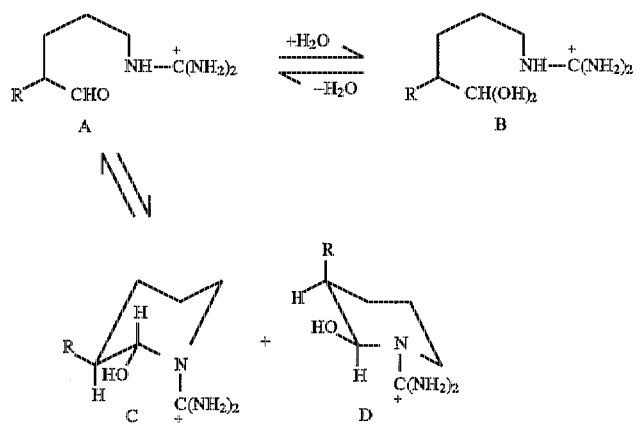

"Hydrophobic group" refers to a group which, when attached to molecules, would cause them to have an aversion to water and cluster together in order to avoid contact with water in an aqueous media. Typically, these include groups containing four or more carbon atoms, as a branched alkyl or alkenyl, and polycyclic alkyl substituents.

In preferred embodiments A is azetidine carboxylic acid, L-proline, β-methyl-L-proline, β,β-dimethyl-L-proline or 3,4-dehydro-L-proline.

In another aspect, the invention features a method for synthesis of a peptide aldehyde. The method includes reacting a semicarbazide having the formula:

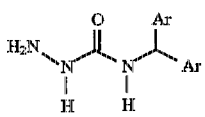

where Ar is optionally substituted phenyl or an equivalent thereof, with an N-protected amino acid aldehyde to produce a protected semi-carbazone, deprotecting the N-terminus of the protected semi-carbazone, and reacting the deprotected semi-carbazone with an N-protected amino acid to produce an N-protected peptide.

In preferred embodiments, the Ar is phenyl; the amino aldehyde is chosen from the group consisting of argininal and lysinal; the deprotecting and reacting the deprotected semi-carbazone steps are repeated a plurality of times with either the same N-protected amino acid or a different N-protected amino acid; the Ar has the formula:

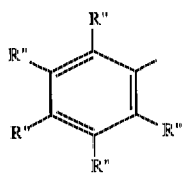
(IV)

where each R" is selected independently from the group consisting of hydrogen, methyl, methoxy, halogen, ethyl and ethoxy.

In yet another aspect, the invention features a protected semi-carbazone formed by reacting a semicarbazide having the formula III above with an α-N-protected amino aldehyde to produce a protected semi-carbazone.

Examples of methods useful for making these semi-carbazides and resulting semi-carbazones are described in Webb, "Reagents for Automated Synthesis of Peptide Analogues," U.S. Ser. No. 07/627,753, filed Dec. 14, 1990 assigned to the same assignee as the present invention, and hereby incorporated by reference herein. See also, Murphy et al., J. Am. Chem. Soc. 114: 3156–3157 (1992).

DETAILED DESCRIPTION OF THE PREFERRED EMBODIMENTS TRYPSIN INHIBITORS

Inhibitors of this invention are generally described above. Below are provided examples of such inhibitors. These examples are not limiting in the invention; those in the art will readily recognize that equivalent inhibitors are synthesized by similar methods to those provided below. For example, one preferred embodiment is the compound, t-butyloxycarbonyl-L-aspartyl-L-prolinyl-L-argininal, which is both a potent and specific inhibitor of trypsin. The inhibitor constant ($K_i$) for this compound against trypsin is $4.5 \times 10^{-10}$M. Moreover, surprisingly little or no inhibition of other serine proteases was found (see Table 2, infra). Another preferred embodiment is the compound of Example 8 which is advantageously specific for inhibiting trypsin.

The specificity of compounds of this invention is unprecedented in the art. For example, McConnell et al., J. Med. Chem., 33: 86 (1989) and Bajusz, Symposia Biologica Hungarica, 25: 277 (1984) report that substitution of the N-terminal acetyl group or hydrogen of leupeptin with a more hydrophobic group, e.g., benzyloxycarbonyl (Cbz) or t-butyloxycarbonyl (Boc) has little effect on trypsin inhibitory activity and specificity or even results in a less potent and nonspecific trypsin inhibitor. Compounds of this invention are generally at least one hundred (100) fold and up to one thousand (1,000) fold or greater, more potent inhibitors of trypsin than the known leupeptin analogs, and show substantially greater specificity.

Synthesis

Compounds of the present invention may be synthesized by either solid or liquid phase methods. The functional groups of the amino acid derivatives used in such syntheses are protected by blocking groups, as described herein, to prevent undesired side-reactions during the coupling procedure. The solution-phase starting materials used are readily available from commercial chemical vendors including Aldrich, Sigma, Nova Biochemicals and the like.

Figure 1:
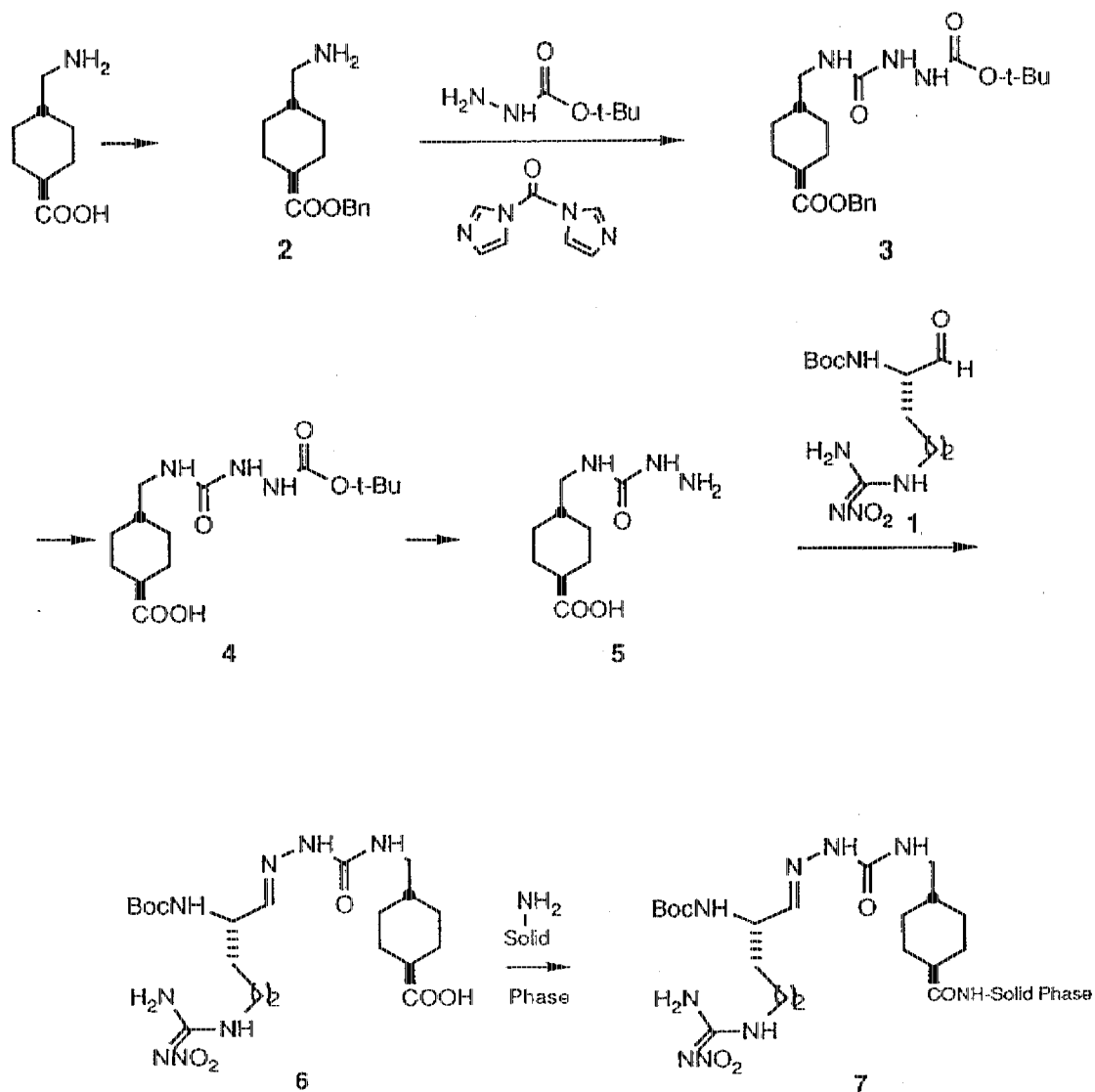
FIG. 1 is a scheme illustrating a process for making a solid phase reagent which is subsequently used to make one or more compounds of the present invention, wherein refers to benzyl, "t-Bu" refers to t-butyl, and "Boc" refers to t-butoxycarbonyl.

The peptide aldehydes can be synthesized by sequential chemical attachment of amino acid derivatives using the solid phase synthesis reagents and methods disclosed by Webb, U.S. patent application, Ser. No. 627,753, filed Dec. 14, 1990, entitled "Reagents for Automated Synthesis of Peptide Analogues," assigned to the same assignee as the present invention, the disclosure of which is incorporated herein by reference. FIG. 1 illustrates the synthesis of a solid phase reagent to which subsequent amino acid derivatives are attached, details of which are provided in the examples, infra.

The present invention also features semicarbazone derivatives discussed above, prepared from the above peptide aldehydes. The semicarbazones are derivatives of the peptide aldehydes which protect the aldehyde functionality of the peptide aldehyde. Unlike the compounds described by McConnell et al., supra, at p. 88, such semicarbazone derivatives are soluble in organic solvents, are crystalline, and couple in high yield, which makes them useful for efficient synthesis of desired peptide aldehydes.

There have been reports of various methods for the solution synthesis of peptide aldehydes (see Bajusz et al., J. Med. Chem. 33: 1729–1735 (1990); McConnell et al., J. Med. Chem. 33: 86–93 (1990) and references cited therein; Kawamura et al., Chem. Pharm. Bull., 17;1902 (1969); Someno et al., ibid, 34, 1748 (1986); Westerik and Wolfenden, J. Biol. Chem., 247: 8195 (1972); and Ito et al., Chem. Pharm. Bull. 23, 3081, (1975)). McConnell et al., supra have used the unsubstituted semicarbazide as an aldehyde protecting reagent for the solution synthesis of peptide aldehydes. Galpin et al., Pept. Struct. Funct., Proc. Am. Pept. Symp., 9th, 799–802 (Edited by: Deber, C., M., Hruby, V., J., Kopple, K., D., Pierce Chem. Co., Rockford, Ill.) have reported on the use of a soluble semicarbazide functionalized polymer which they have used for the manual preparation of some peptide aldehydes.

The methods cited above have significant limitations in scope and practical utility. Only a few of these methods have been shown to be applicable to the synthesis of peptide argininals. The procedures that use lithium aluminum hydride to generate the peptide aldehyde at a late stage in the synthesis (see Bajusz et al., supra) are not applicable to the synthesis of derivatives containing ester protecting groups or other functional groups sensitive to lithium aluminum hydride (LiAlH$_4$). Therefore the hydride procedure is not suited for the synthesis of derivatives containing, for example, aspartic acid or glutamic acid when this reaction sequence is used. Procedures that use the unsubstituted semicarbazide group as a protecting group for the argininal (see McConnell et al., cited above) suffer from low yields and significant solubility problems. The procedures for the solid phase automated synthesis of peptide aldehyde analogs described in the commonly assigned U.S. patent application, Ser. No. 07/627,753, filed Dec. 14, 1990, has overcome many of these problems. However, under certain circumstances, for example, in the case of large scale synthesis, due to cost considerations, the use of the solution phase methods described herein may be particularly advantageous.

Figure 3:
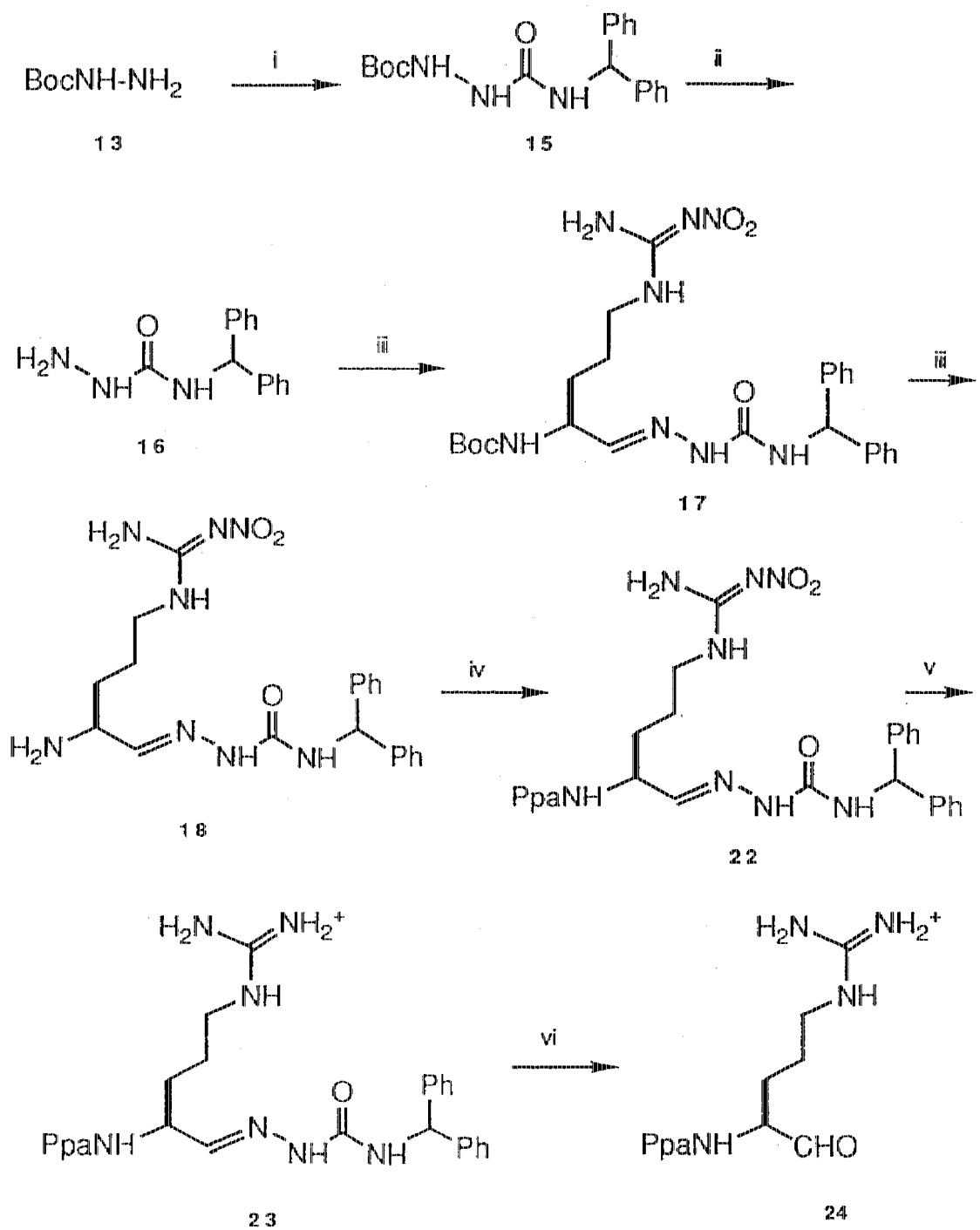
FIG. 3 is a scheme illustrating a process for synthesis of compound 24, wherein "i" refers to CDI/13 followed by 14, "ii" refers to TFA/DCM, "iii" refers to 1/sodium acetate, "iv" refers to a protected peptide or analog as free acid (Ppa), e.g., 21 of FIG. 2/BOP/NMM/DMF, "v" refers to H$_2$/Pd, and "vi" refers to H$_3$O$^+$.

We have therefore devised a new protecting group that has many advantages over the existing aldehyde protecting group. The procedure for the synthesis of this protecting group (the 4-diphenylmethyl-semicarbazide group or DPS group) and its use for the preparation of peptide aldehydes, is illustrated in FIG. 3. The DPS group has many advantages over the simple semicarbazide group; including the much greater solubility of the resulting DPS semicarbazone derivatives; also, many of the intermediates are crystalline and can be purified by simple recrystallization. The intermediates also give good yields on coupling and deprotection, etc.

The commercially available 4-phenylsemicarbazide was also investigated by us as a potential aldehyde protecting group reagent. Using this reagent some protected argininals were converted to the corresponding 4-phenylsemicarbazones. Although these derivatives do not have sufficient solubility to be a practical alternative to the DPS derivatives, the 4-phenylsemicarbazones do offer some advantages over the simple semicarbazones.

Formulations

The present invention also includes the pharmaceutically acceptable salts of the compounds disclosed. These salts include acid addition salts, for example, salts of hydrochloric, hydrobromic, acetic acid, and benzene sulfonic acid; other suitable acid addition salts are considered to be within the scope of this invention.

The present invention also includes compositions prepared for storage or administration which include a pharmaceutically effective amount of the disclosed compounds in a pharmaceutically acceptable carrier or diluent. Acceptable carriers or diluents for therapeutic use are well known in the pharmaceutical art, and are described, for example, in *Remington's Pharmeceutical Sciences,* Mack Publishing Co. (A. R. Gennaro edit. 1985) hereby incorporated by reference herein. For example, preservatives, stabilizers, dyes and even flavoring agents may be provided. Id. at 1449. These include sodium benzoate, sorbic acid and esters of p-hydroxybenzoic acid. In addition, antioxidants and suspending agents may be used. Id.

A pharmaceutically effective dose of the composition required for the prevention or treatment of pancreatitis will depend on the route of administration, the type of mammal being treated, and the physical characteristics of the specific mammal under consideration. The compositions of the present invention may be formulated and used as tablets, capsules or elixirs for oral administration; suppositories for rectal administration; sterile solutions, suspensions for injectable administration, and the like. The dose and method of administration can be tailored to achieve optimal efficacy but will depend on such factors as weight, diet, concurrent medication and other factors which those skilled in the medical arts will recognize. Generally, an amount between 0.1 mg/kg and 100 mg/kg body weight/day is administered dependent upon potency of the inhibitor.

The potency and specificity of the compounds of the present invention are determined by in vitro assay methods well known in the art. Potency is assessed from the concentration of compound required to substantially inhibit the enzymatic action of trypsin. Specifically, the inhibitor constant, $K_i$, of the compounds can be determined by the method of Dixon, Biochem. J. 55: 170 (1953). The specificity is assessed by determination of the concentration, $IC_{50}$, of compound required to give 50% inhibition of the enzymatic activity of the coagulation enzymes, kallikrein, factor XIa, factor VIIa, factor Xa, thrombin; the fibrinolysis enzymes, plasmin, tissue plasminogen activator (tPA), and urokinase (UK), and the anticoagulation enzyme, protein C. Specificity is found when the concentration of compound giving 50% inhibition of trypsin is low relative to the concentration required to give like inhibition of the other enzymes. That is, the $IC_{50}$ for trypsin should be less than abut 0.1, preferably 0.01 μM, while the $IC_{50}$ for the other enzymes is at least 10–1000 fold (preferably 10–100 fold) greater, e.g., greater than 1 μM.

The efficacy of the compounds of the present invention as a prophylactic treatment for pancreatitis is assessed in vivo using the chemically-induced animal model of Niederau et al., Gastroenterology 88: 1192–1204 (1985).

The compounds of the present invention, as selected by the in vitro and in vivo methods disclosed, are potent and highly specific inhibitors of trypsin and thus are useful for the prevention and treatment of pancreatitis in mammals.

The invention will now be further illustrated by the following examples. Unless otherwise specified, the procedures described in the following examples are conducted at ambient temperature and pressure. The first seven examples are illustrated in FIG. 1.

EXAMPLE 1

Preparation of α-N-t-butoxycarbonyl-$N^g$-nitro-argininal

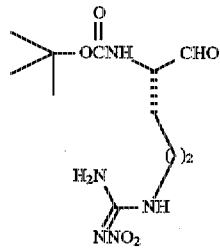

The following procedure for the synthesis of alpha-t-butoxycarbonyl-$N^g$-nitro-argininal 1 is an example of a general procedure for the preparation of Boc-amino acid aldehydes. See Patel et al., Biochim. Biophys. Acta, 748, 321–330 (1983). 12.7 g Boc-$N^g$-nitro-arginine (40 mmoles) and 7.0 g carbonyldiimidazole (CDI; 43 moles) were added at room temperature (between 20 and 25° C.) to 200 mL dry tetrahydrofuran (THF) and allowed to stir for 30 minutes. The reaction mixture was cooled to −78° C. and 35 mL LiAlH$_4$ (1 M in THF) was added dropwise over thirty minutes. The reaction was allowed to stir for an additional 1 hour at −78° C. Next, 18 mL acetone was added and the mixture quickly added to 400 mL 1N HCl. The mixture was extracted twice with 100 mL ethyl acetate. The ethyl acetate washes were combined and then washed two times each with 100 mL water, 100 mL saturated NaHCO$_3$ and 100 mL saturated NaCl (brine). The solution was dried using MgSO$_4$ and concentrated to a foam. The crude weight of the alpha-t-butoxycarbonyl-$N^g$-nitro-arginal was 6.36 g (21 mole; yield 52%).

The following alternative procedure for the synthesis of alpha-t-butoxycarbonyl-$N^g$-nitro-argininal 1 is a modification of the procedure of Fehrentz and Castro, Synthesis, 676 (1983).

Boc-$N^g$-nitro-arginine was obtained from Calbiochem. N-methyl piperidine, N,O-dimethylhydroxylamine hydrochloride and isobutylchloroformate, and lithium aluminum hydride were obtained from Aldrich Chemical Company, Inc. Dichloromethane, ethyl acetate, methanol and tetrahydrofuran may be obtained from Fisher Scientific Company.

11.4 mL N-methyl piperidine was slowly added to a stirred suspension of 8.42 g (94 mmole) N,O-dimethylhydroxylamine in 75 mL dichloromethane which had been cooled to about 0° C. The solution was allowed to stir for 20 minutes to give the free hydroxylamine, and then was kept-cold for use in the next step.

In a separate flask, 30.0 g (94 mmole) Boc-$N^g$-nitroarginine was dissolved by heating in abut 1400 mL tetrahydrofuran and cooled under nitrogen to 0° C. 11.4 mL N-methylpiperidine and 12.14 mL (94 mmole) isobutylchloroformate was added and the mixture stirred for 10 minutes. The free hydroxylamine prepared above was added all at once, the reaction mixture allowed to warm to room temperature, and then stirred overnight.

The resulting precipitate was filtered off, then washed with 200 mL tetrahydrofuran. After concentrating the filtrates to about 150 mL under vacuum, 200 mL ethyl acetate was added, followed by ice to cool the solution. The cooled solution was washed with two 75 mL portions of 0.2N hydrochloric acid, two 75 mL portions 0.5N sodium hydroxide, and one 75 mL portion brine, and then dried over anhydrous magnesium sulfate. Upon concentration in vacuum, 22.7 g (70% yield) of solid Boc-Ng-nitro-arginine N-methyl-O-methylcarboxamide was recovered. Thin layer chromatographic analysis in 9:1 dichloromethane/methanol (silica gel) showed one spot.

A flask was placed under a nitrogen atmosphere and cooled to −50° C., then charged with 70 mL (70 mmole) 1N lithium aluminum hydride (in tetrahydrofuran) and 500 mL dry tetrahydrofuran. 50mL of a solution containing 66 mmole BoC-$N^g$-nitroarginine N-methyl-O-methylcarboxamide in dry tetrahydrofuran was slowly added while the temperature of the reaction mixture was maintained at −50° C. After allowing the reaction mixture to warm to 0° C. by removal of the cooling, it was recooled to −30° C., at which temperature 100 mL (0.2 mole) 2N potassium bisulfate was added with stirring over about a 10 to 15 minute period. The reaction mixture was then allowed to stir at room temperature for 2 hours. After filtering off the precipitate, the filtrate was concentrated to 100 mL under vacuum. The concentrate Was poured into 800 mL ethyl acetate, then was washed successively with two 50 mL portions 1N hydrochloric acid, two 50 mL portions saturated sodium bicarbonate, one 50 mL portion brine. The combined aqueous extracts were extracted with 3–100 mL portions of ethyl acetate. All of the ethyl acetate washes were combined and then dried over anhydrous magnesium sulfate. The mixture was concentrated under vacuum to yield 18.5 g (95%) compound 1.

EXAMPLE 2

Preparation of trans-4-(aminomethyl)-cyclohexane carboxylic acid benzyl ester para-toluenesulfonate salt

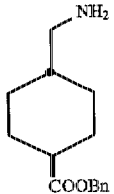

2

50 g (0.318 moles) trans-4-(aminomethyl)-cyclohexane carboxylic acid, 61.7 g (0.324 moles) p-toluenesulfonic acid, 250 mL (2.4 moles) benzyl alcohol, and 250 mL toluene were combined and stirred at room temperature. The mixture was refluxed for 24 hours and the liberated water removed azeotropically by means of a Dean and Stark apparatus. A clear solution was obtained after 5 hours of refluxing. The solution was allowed to cool to room temperature and the product crystallized. The mixture was vacuum filtered, washed with ether and dried in a vacuum oven to give 128.12 g (96% yield). $^1$H NMR (CD$_3$OD) δ 1.05 (m, 2H), 1.43 (m, 2H), 1.59 (m, 1H) 1.85 (m, 2H), 2.03 (m, 2H), 2.33 (m, 1H), 2.35 (s, 3H), 2.75 (d, 2H), 5.09 (s, 2H), 7.23 (d, 2H), 7.32 (m, 5H), 7.69 (d, 2H). M.P. 154°–156° C. See, Greenstein and Winitz, Chemistry of the Amino Acids. 2: 942 (1986).

EXAMPLE 3

Preparation of 1-t-butoxycarbonyl-semicarbazidyl-trans-4-methyl cyclohexane carboxylic acid benzyl ester

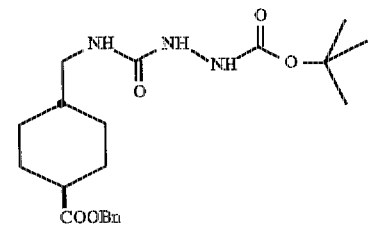

3

3.24 g (0.02 moles) carbonyldiimidazole (CDI) was dissolved in 45 mL of dimethylformamide (DMF) at room temperature under nitrogen. A solution of 2.48 g (0.02 moles) t-butyl carbazate in 45 mL DMF was added dropwise. 8.38 g (0.02 moles) solid benzyl ester 2 was added, followed by the dropwise addition of 3.06 mL triethylamine (TEA) over a 30 minute period. The reaction was allowed to stir at room temperature under nitrogen for one hour. Water (100 mL) was added and the mixture extracted three times with 50 mL ethyl acetate. The ethyl acetate layers were combined and extracted two times each with 75 mL 1N HCl H$_2$O, NaHCO$_3$, NaCl and dried with MgSO$_4$. The mixture was filtered and the solution was concentrated to give an oil. This material could be purified by recrystallization from ethyl acetate/hexanes (M.P.=106°–108° C.) or used directly in the next step. $^1$H NMR (CDCl$_3$) δ 0.94 (m, 2H), 1.42 (m, 2H), 1.45 (s, 9H), 1.81 (m, 2H), 2.02 (m, 2H), 2.27 (m, 1H), 3.17 (t, 2H), 5.09 (s, 2H), 5.51 (t, 1H), 6.46 (s, 2H), 7.34 (m, 4H).

EXAMPLE 4

Preparation of 1- (t-butoxycarbonyl)-3-semicarbazidyl-trans-4-methyl-cyclohexane carboxylic acid

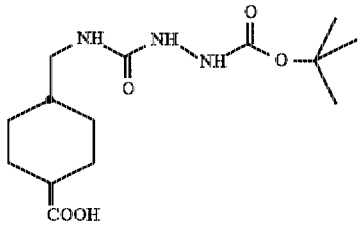

5 To the crude Boc-benzyl ester 3 from Example 3 above, 250 mL of methanol (MeOH) and 500 mg of 10% palladium on activated carbon were added. After shaking on the hydrogenator for one hour at 5 psig $H_2$, the mixture was filtered with Celite through a fine fritted filter. The solution was concentrated to a foam, methylene chloride added, and a precipitate formed. The mixture was kept at 5° C. for 65 hours. The crystallized material was filtered with ether and 4.0 g of crude product obtained (12.7 mmoles; yield 62% overall yield from compound 2.) $^1$H NMR ($CD_3OD$), δ 0.96, (m, 2H), 1.42 (m, 2H), 1.46 (s, 9H), 1.82 (m, 2H), 1.97 (m, 2H), 2.18 (m, 1H), 3.0 (t, 2H). M.P.=185°–189° C.

EXAMPLE 5

Preparation of semicarbazidyl-trans-4-methylcyclohexane carboxylic acid trifluoroacetate salt

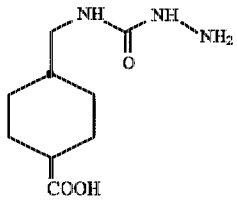

315 mg (1 mmole) of compound 4 was added to 10 mL trifluoroacetic acid (TFA) at 0° C. and the resulting solution stirred for 30 min. After this time the solution was added dropwise to 75 mL ether. A precipitate formed, and the mixture was filtered and washed with ether. Weight of crude product was 254 mg, 0.77 mmoles; yield (77%). $^1$H NMR ($CD_3OD$), δ1.0 (m, 2H), 1.38 (m, 2H), 1.43 (m, 1H), 1.84 (m, 2H), 2.01 (m, 2H), 2.22 (m, 1H), 3.04 (d, 2H). M.P.=154°–156° C.

EXAMPLE 6

Preparation of a- (t-butoxycarbonyl) -$N^g$-nitro argininal-semicarbazonyl-trans-4-methylcyclohexane carboxylic acid

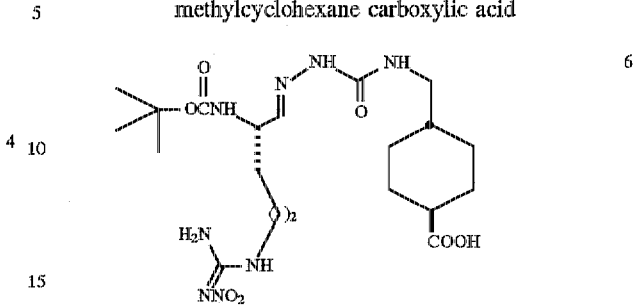

A solution of 13.7 g (41.6 mmoles) compound 5, 18.0 g (~59 mmoles) crude compound 1 in 135 mL ethanol containing 45 mL water, was treated with 9.41 g (69 mmoles) NaOAc and refluxed for one hour. This solution was allowed to cool and then poured into 0.1N HCl and extracted three times with ethyl acetate. The combined organic phase was washed with water, then brine, dried with $MgSO_4$ and concentrated to a small volume. This cloudy mixture was allowed to set overnight at 5° C. to precipitate the product, which was isolated by filtration and dried under vacuum. This gave 9.9 g, 47% yield based on 5. $^1$H NMR ($CD_3OD$), δ 1.0 (m, 2H), 1.43 (s, 9H), 1.45–2.20 (m, 13H), 3.09 (d, 2H), 3.30 (m, 2H), 4.18 (bs, 1H), 7.10 (d, 1H). M.P. =162°–163° C.

EXAMPLE 7

Synthesis of Semicarbazide Solid Support

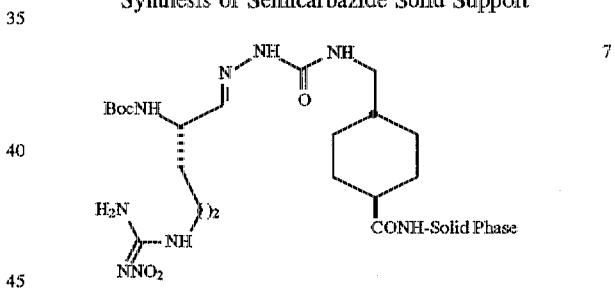

Solid phase reagent 7 was prepared by placing 0.8 g (0.5 mmoles, 0.62 g/mol) methyl-benzhydrylamine (MBHA) resin in a reaction vessel and washing 1 time with dichloromethane (DCM) (all washes require 10 mL of solvent with agitation for 1–2 minutes), 3 times with dimethylformamide (DMF), 2 times with 10% diisopropylethylamine (DIEA)/DMF, and 4 times with DMF. 5 mL DMF, 1 mmole 4-methylmorpholine (NMM) (102 µl), 1 mmole benzotriazol-1-yloxy-tris-(dimethylamino)-phosphonium-hexa-fluorophosphate (BOP reagent), (443 mg), and 1 mmole compound 6 (500 mg) was added, mixed on a rotating wheel for 16 hours, and washed 3 times with DMF, 2 times with 10% DIEA/DMF and 3 times with DMF. The resin was then washed successively with DCM, methanol, and ether.

The resulting resin 7 shows 98–99% coupling yield by ninhydrin.

This resin was then extended at the N-terminus, with amino acids or amino acid analogs, on a conventional peptide synthesizer using standard t-Boc methodology as shown in the examples which follow.

The automated synthesis of peptide aldehydes was performed on an Applied Biosystems model 430A peptide synthesizer using the t-Boc chemistry conditions in the 430A user's manual. The resulting protected peptide aldehyde can be cleaved from support with formaldehyde and deprotected with hydrogen/Pd. The nitro group can be removed from the guanidine group without reduction of the aldehyde.

EXAMPLE 8

Preparation of N-t-butyloxycarbonyl-L-Glu-L-Pro-L-argininal

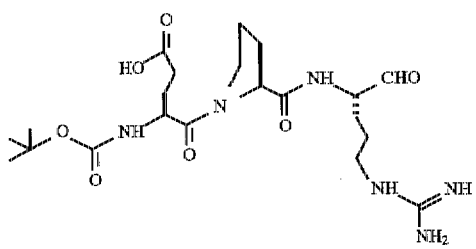

The peptide aldehyde 8 was synthesized using an Applied Biosystems Model 430A peptide synthesizer as discussed above. The t-Boc chemistry conditions utilized were as provided in the instrument user's manual.

0.500 g resin 7 was made ready for use by removing the t-Boc protecting groups by treatment with 50% trifluoroacetic acid (in dichloromethane). After washing and neutralizing the acidity by treatment with 10% diisopropylethylamine (in dichloromethane), commercially available t-Boc-protected amino acids were coupled to the support reagent (and the growing amino acid support chain) in a sequential manner.

Thus, N-Boc-L-proline was attached to the resin using dicyclohexylcarbodiimide and 1-hydroxybenztriazole in dimethylformamide, followed by treatment with 50% trifluoroacetic acid (in dichloromethane) to remove the tBoc protecting group, a wash step and a wash with 10% diisopropylethylamine (in dichloromethane) to neutralize acidity. N-Boc-L-glutamic acid-γ-benzyl ester was coupled in the same manner, except that treatment with 50% trifluoroacetic acid was omitted.

The peptide aldehyde was removed from the solid phase by treatment with a mixture of 5 mL tetrahydrofuran, 1 mL acetic acid, 1 mL formaldehyde and 0.100 mL 1N HCl for 1 hour with stirring. After filtering this mixture, the resin was washed with 10 mL of tetrahydrofuran. The combined filtrates were diluted with 100 mL water and extracted with ethyl acetate. The ethyl acetate phase was then washed with saturated NaCl, dried over magnesium sulfate, and concentrated under vacuum.

To remove the nitro and benzyl protecting groups of the peptide aldehyde, the concentrated peptide aldehyde was taken up in a mixture comprising 10 mL of 10% water in methanol, 0.300 mL 1N HCl and 0.200 g palladium on carbon, and then treated with hydrogen at 5 psi for 45 minutes. The mixture was filtered through a fine fritted filter with Celite, washed with 10% water in methanol, and concentrated to give the crude peptide aldehyde.

The resulting peptide aldehyde was then purified using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield product 8. Fast atom bombardment mass spectrometry gave observed molecular weight of 484 a.m.u.; calculated molecular weight was 484 a.m.u.

EXAMPLE 9

Preparation of N-t-butyloxycarbonyl-L-Asp-L-Pro-L-argininal

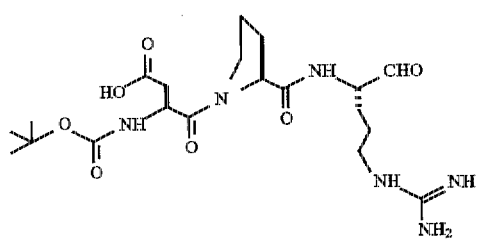

Peptide aldehyde 9 was synthesized and purified in the same manner as described in Example 8. Here, N-Boc-L-proline was first attached to resin 7 followed by N-Boc-L-aspartic acid-beta-benzyl ester (in the place of N-Boc-L-glutamic acid-γ-benzyl ester). Again, treatment with 50% trifluoroacetic acid was omitted after the last coupling. Fast atom bombardment mass spectrometry gave observed molecular weight of 470 a.m.u.; calculated molecular weight was 470 a.m.u.

EXAMPLE 10

Preparation of N-isobutyloxycarbonyl-L-Asp-L-Pro-L-argininal

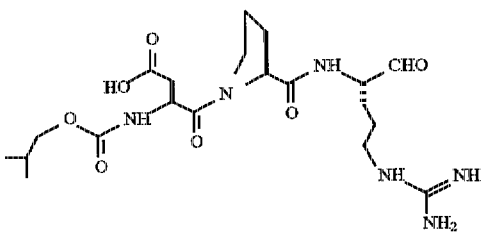

Peptide aldehyde 10 was synthesized and purified in the same manner as described in Example 8. Here, N-Boc-L-proline was first attached to resin 7 followed by N-isobutoxycarbonyl-L-aspartic acid-beta-benzyl ester (in the place of N-Boc-L-glutamic acid-γ-benzyl ester). Again, treatment with 50% trifluoroacetic acid was omitted after the last coupling. Fast atom bombardment mass spectrometry gave observed molecular weight of 470 a.m.u.; calculated molecular weight was 470 a.m.u.

EXAMPLE 11

Preparation of N-adamantyloxycarbonyl-L-Asp-L-Pro-L-argininal

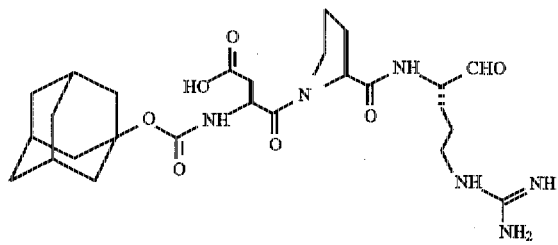

2.5 g (12.6 mmole) adamantyloxycarbonyl fluoride was added to a mixture of 2.2 g (10 mmole) α-N-(t-butoxycarbonyl) -L-aspartic acid-beta-(benzyl ester) in 50 mL saturated NaHCO$_3$ and 30 mL tetrahydrofuran. After stirring for 2 hours at room temperature, the reaction mixture was poured into 100 mL 1N hydrochloric acid, and extracted with ethyl acetate. The combined extracts were washed with water, dried over MgSO$_4$, and concentrated to an oil. The oil was taken up in ether, then precipitated by addition of hexanes. The supernatant was decanted and the liquid concentrated in vacuum to give a white foam. 1.8 g (45% yield) N-adamantyloxycarbonyl-L-aspartic acid-gamma-benzyl ester was recovered.

Peptide aldehyde 11 was synthesized and purified in the same manner as described in Example 8.

Here, N-Boc-L-proline was first attached to resin 7 followed by N-adamantyloxycarbonyl-L-aspartic acid-gamma-benzyl ester (in the place of N-Boc-L-glutamic acid-γ-benzyl ester). Again, treatment with 50% trifluoroacetic acid was omitted after the last coupling. Fast atom bombardment mass spectrometry gave observed molecular weight of 548 a.m.u.; calculated molecular weight was 548 a.m.u.

EXAMPLE 12

Preparation of N-t-butyloxycarbonyl-D-Asp-L-Pro-L-argininal

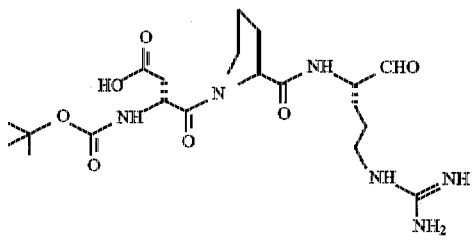

Peptide aldehyde 12 was synthesized and purified in the same manner as described in Example 8. Here, N-Boc-L-proline was first attached to resin 7 followed by N-Boc-D-aspartic acid-beta-benzyl ester (in the place of N-Boc-L-glutamic acid-γ-benzyl ester). Again, treatment with 50% trifluoroacetic acid was omitted after the last coupling. Fast atom bombardment mass spectrometry gave observed molecular weight of 470 a.m.u.; calculated molecular weight was 470 a.m.u.

Figure 2:
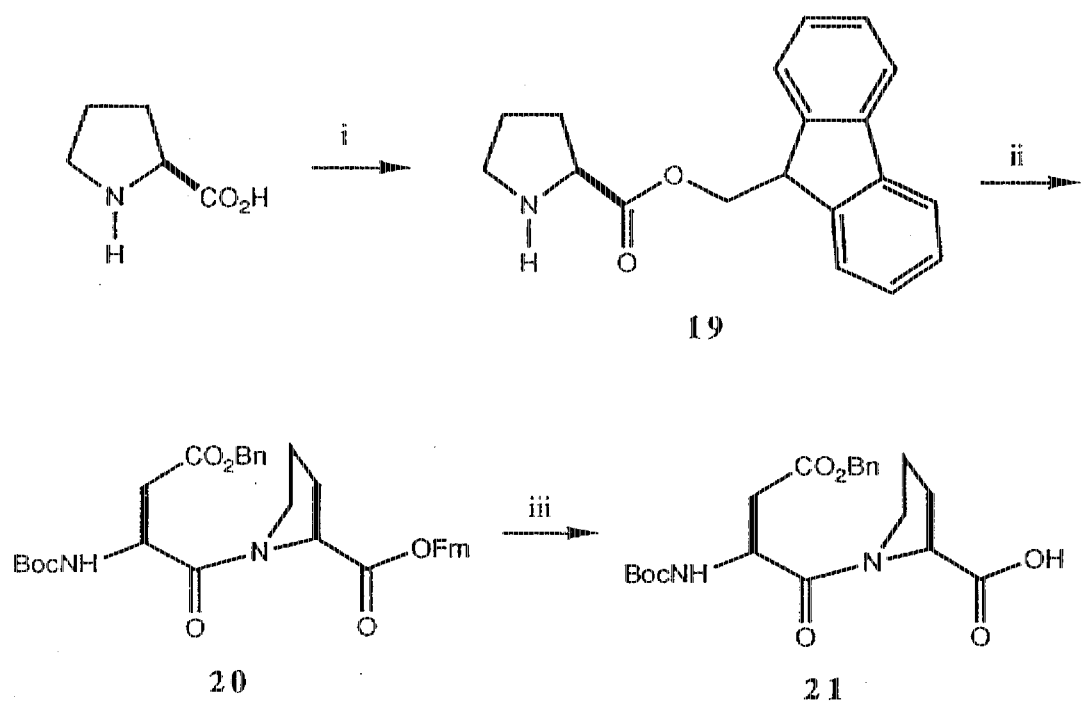
FIG. 2 is a scheme illustrating a process for synthesis of compound 21, wherein "i" refers to pTsOH/FmOH, tolulene/ reflux, "ii" refers to Boc-Asp-β-benzyl ester/BOP/NMM/ DMF and "iii" refers to triethylamine/reflux.

In the following examples the $^1$H NMR is consistent with the desired product in every case. The following examples are illustrated in FIGS. 2 and 3.

EXAMPLE 13

Preparation of 1-t-butoxycarbonyl-semicarbazidyl-4-diphenylmethane

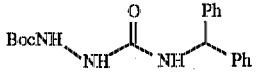

A solution of 16.2 g (0.10 mole) carbonyldiimidazole (CDI) in 225 mL dimethylformamide (DMF) was prepared at room temperature and allowed to stir under nitrogen. A solution of 13.2 g (0.100 moles) t-butyl carbazate (13) in 225 mL DMF was then added dropwise over a 30 min. period. Next a solution of 18.3 g (0.10 moles) diphenylmethylamine 14 in 100 ml DMF was added over a 30 min. period. The reaction was allowed to stir at room temperature under nitrogen for one hour. Water (10 mL) was added and the mixture concentrated to about 150 mL under vacuum. This solution was poured into 500 mL water and extracted with 400 mL ethyl acetate. The ethyl acetate phase was extracted two times each with 75 mL 1N HCl, H$_2$O, saturated NaHCO$_3$, and brine, and dried with MgSO$_4$. The mixture was filtered and the solution was concentrated to give 29.5 g (85% yield) of a white foam. This material could be purified by recrystallization from ethyl acetate/hexane, but was pure enough to use directly in the next step: mp 142–143° C. Anal. Calcd. for C$_{19}$H$_{23}$N$_3$O$_3$: C, 66.84; H, 6.79; N, 12.31. Found: C, 66.46; H, 6.75; N; 12.90.

EXAMPLE 14

Preparation of semicarbazidyl-4-diphenylmethane trifluoroacetate salt

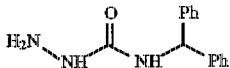

A solution of 3.43 g (10 mmole) compound 15 in 12.5 mL dichloromethane was treated with 12.5 mL of trifluoroacetic acid (TFA) at 0° C. and allowed to stir for 30 min at this temperature. After this time the solution was added dropwise to 75 mL ether. A precipitate formed, and the mixture was filtered and washed with ether. Weight of crude product was 2.7 g (80% yield): mp 182°–184° C.

EXAMPLE 15

Preparation of α-N-(t-butoxycarbonyl-N$^g$-nitro-argininal-semicarbazonyl-4-N-diphenylmethane

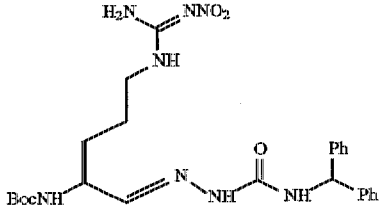

A solution of 2.65 g (7.8 mmoles) compound 16, and 2.36 g (7.8 mmoles) of 1 (alpha-N-(t-butoxycarbonyl)-N$^g$-nitro-argininal) in 20 mL ethanol containing 6 mL of water, was treated with 1.2 g (8.8 moles) of sodium acetate and refluxed for one hour. This solution was allowed to cool and then poured into water and extracted three times with ethyl acetate. The combined organic phase was washed with water, 0.1N HCl, and brine, dried with MgSO₄, and concentrated to a small volume. The white solid residue was recrystallized from acetonitrile/ether. This gave 3.2 g (78% yield base on 16): mp 78–79° C.

EXAMPLE 16

Preparation of N^g-nitro-argininal-semicarbazonyl-4-N-diphenylmethane trifluoroacetate salt

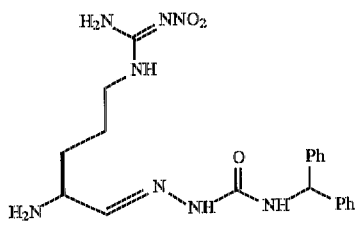

18

A solution of 0.53 g (1.0 mmole) compound 17 in 5 mL dichloromethane was treated with 5 mL trifluoroacetic acid (TFA) at 0° C. and allowed to stir for 30 minutes at this temperature. After this time the solution was added dropwise to 40 mL ether. A precipitate formed, and the mixture was filtered and washed with ether. This gave 0.51 g of a pure white solid (97% yield): mp 159°–160° C.

EXAMPLE 17

Preparation of L-proline-9fluorenemethyl ester p-toluenesulfonic acid salt

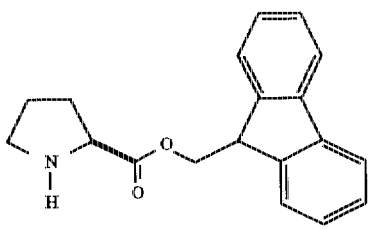

19

A solution of L-proline 15.99 g (139.0 mmole), 9-fluorenemethanol 30.0 g (152.9 mmole), and p-toluenesulfonic acid in 600 mL of toluene was refluxed and water was removed with a Dean-Stark trap. After 26 hours, the reaction was concentrated to give 64 g (99% crude yield) of an oil which was used directly in the next step.

EXAMPLE 18

Preparation of α-N-(t-butoxycarbonyl)-L-aspartyl-beta-(benzyl ester) -L-proline-9-fluorenemethyl ester

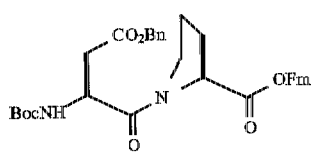

20

A solution of L-proline-9-fluorenemethyl ester p-toluenesulfonic acid salt 19 (15.44 g, 33.2 mmole), α-N-(t-butoxycarbonyl) -L-aspartic acid-beta-(benzyl ester) (9.35 g 41.9 mmole), benzotriazol-1-yloxy-tris-(dimethylamino)-phosponium-hexafluorophosphate (BOP reagent) 18.6 g (42.0 mmole) in 100 mL DMF was allowed to stir in an ice-bath. This solution was treated with 1-hydroxybenzotriazole hydrate (0.45 g, 3.34 mmole), diisopropylethylamine (19.0 mL, 198 mmole) and the reaction allowed to stir at 0°–5° C. for 1.5 hours. After this time the reaction mix was poured into 600 mL of ethyl acetate and extracted successively with saturated aqueous citric acid, water, saturated sodium bicarbonate, and finally brine. The organic phase was dried with MgSO₄ and concentrated under vacuum to give 18 g (91% crude yield) of an oil, which was used directly in the next step.

EXAMPLE 19

Preparation of α-N-(t-butoxycarbonyl)-L-aspartyl-beta-(benzyl ester) -L-proline

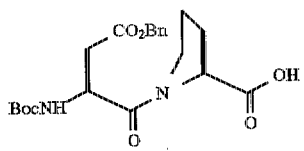

21

The crude oil from above, α-N-(t-butoxycarbonyl)-L-aspartyl -beta-(benzyl ester)-L-proline 9-fluorenemethyl ester 20 (17.5 g, 29.2 mmole) was suspended in 250 mL triethylamine and allowed to reflux for 1 hour. This mixture was concentrated to an oil, dissolved in 600 mL of ethyl acetate. The ethyl acetate phase was washed once with citric acid, once with brine, dried with MgSO₄, and concentrated to give an oil. This material was purified by column chromatography (silica gel, 10–20% THF/DCM) to give 7.5 g (38% overall from 19).

EXAMPLE 20

Preparation of α-N-(t-butoxycarbonyl)-L-aspartyl-beta-(benzyl ester) -L-prolyl-L-N^g-nitro-argininal-semicarbazonyl-4-N-diphenylmethane

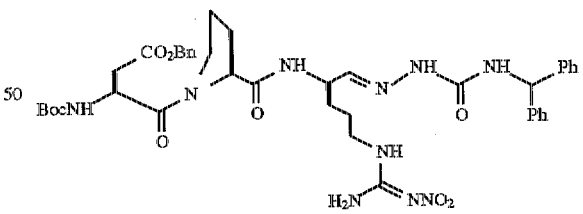

22

α-N-(t-butoxycarbonyl)-L-aspartyl-beta-(benzyl ester)-L-proline 21 (11.29 g, 26.9 mmole) was dissolved in 60mL DMF. This solution was treated with N-methylmorpholine (NMM, 11.9 mL, 108 mole), BOP (11.9 g, 27 mole) and 18 (14.64 g, 28 mmole), then allowed to stir for 2h. This mixture was poured into 700 mL ethyl acetate and washed with 1N citric acid, saturated NaHCO₃, water, and brine, dried with MgSO₄, and concentrated to give a foam. This material was purified by column chromatography (silica gel, 6–20% IPA/DCM) to give 12.5 g (38% overall from 21).

EXAMPLE 21

Preparation of α-N-(t-butoxycarbonyl)-L-aspartyl-L-prolyl-L-argininal

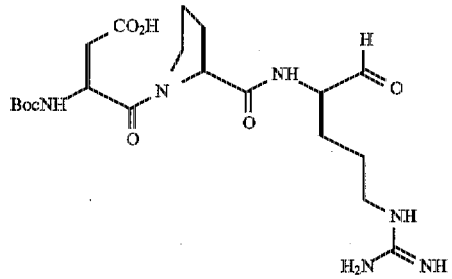

23

A solution of 22 (4.4 g, 5.1 mmole) in 85 mL methanol was treated with 20 mL water, 10.5 mL glacial acetic acid, 44 mL 1N HCl, and 2.2 g 10% Pd on carbon. This was hydrogenated at 11 psi with shaking for 70 min. The mixture was filtered and concentrated to a small volume. The resulting peptide aldehyde was then purified using reverse phase HPLC on a 10 micron particle size, 300 angstrom pore size C-18 column, eluting with a water-acetonitrile (both containing 0.01% trifluoroacetic acid) gradient, where the gradient ran from 5% to 40% acetonitrile. The column fractions were analyzed by analytical HPLC and fractions containing pure product were pooled and lyophilized. This gave 400 mg of pure 23, which was identical to the product from Example 9, along with 1.2 g of debenzylated starting material. The yield was 25% based on consumed starting material.

EXAMPLE 22

Preparation of N-t-butyloxycarbonyl-L-(β-methyl ester)-Asp-L -Pro-L-argininal

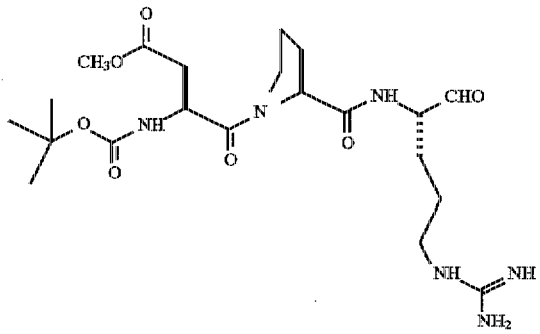

24

Peptide aldehyde 24 is synthesized and purified in the same manner as described in Example 8. Here, N-BOC-L-proline is first attached to resin 7 followed by N-BOC-L-(β-methyl ester) aspartic acid in the place of N-Boc-L-glutamic acid-γ-benzyl ester. Again, treatment with 50% trifluoroacetic acid is omitted after the last coupling.

EXAMPLE 23

Preparation of N-t-butyloxycarbonyl-L-(βt-butyl ester) -Asp-L -Pro-L-argininal

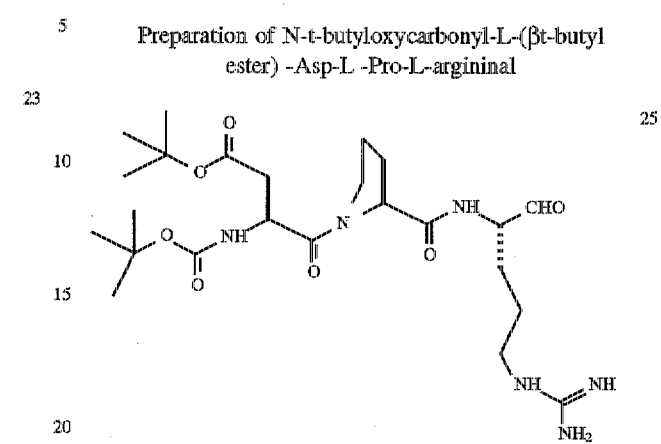

25

Peptide aldehyde 25 is synthesized and purified in the same manner as described in Example 8. Here, N-Boc-L-proline is first attached to resin 7 followed by N-Boc-L-(β-t-butyl ester) aspartic acid in the place of N-Boc-L-glutamic acid-γ-benzyl ester. Again, treatment with 50% trifluoroacetic acid is omitted after the last coupling.

EXAMPLE 24

Preparation of 3-Cyano-2-(1,1-dimethylethoxy) methanamidopropionic acid

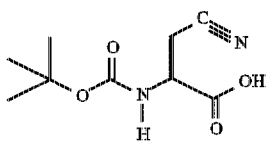

26

20.0 g (86 mmol, 1 equiv.) of Boc-L-Asparagine (from Bachem or Sigma) was dissolved in 120 mL of dry pyridine and 20.0 g (97 mmol, 1.3 equiv. ) of dicyclohexylcarbodiimide dissolved in 60 mL of dry pyridine was added dropwise over a period of 30 minutes. The reaction was stirred for 3 hours at 23° C. and filtered through a 2μm nylon filter. The filtrate was concentrated in vacuo on a rotary evaporator and 100 ml of water was added. The pH was adjusted to 10 with 40% sodium hydroxide (aq.) and the solution filtered through a 2 μm nylon filter once again. The filtrate was passed through a 120 mL bed of Dowex 50X8-400 ion exchange resin and the resin washed with four column volumes of 1:1 methanol:water. The filtrate was concentrated in vacuo to yield 17.5 g (95% yield) of product as a white solid. $^1$H-NMR (CD$_3$OD): 4.40 p.p.m (m, 1H); 2.95 p.p.m. (m, 2H); 1.40 p.p.m. (s, 9H).

EXAMPLE 25

Preparation of 3-Tetrazolyl-2-(1,1-dimethylethoxy) methanamidopropionic acid

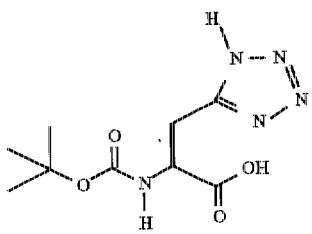

27

17.5 g (82 mmol, 1 equiv.) of 3-cyano-2-(1,1-dimethylethoxy) methanamido-propionic acid 26 was dissolved in 125 mL of tetrahydrofuran and 40.5 g (129 mmol, 1.5 equiv.) tributyltin azide was added. The reaction mixture was brought to reflux and held there for 3 days. The reaction mixture was cooled and the volatiles removed in vacuo on a rotary evaporator. The residue was dissolved in 300 mL of 0.5M sodium hydroxide and this aqueous solution was washed with ethyl acetate (4×100 mL). The aqueous layer was passed through a 125 mL bed of Dowex 50X8-400 ion exchange resin and the resin washed with four column volumes of 1:1 methanol:water. The volatiles were removed in vacuo on the rotary evaporator to yield 17.9 g of the product as a white solid (85 % yield). $^1$H-NMR (CD$_3$OD): 4.55 p.p.m (m, 1H); 3.40 p.p.m. (m, 2H); 1.40 p.p.m. (s, 9H). This material is suitable for use in solid-phase peptide synthesis.

EXAMPLE 26

Preparation of 3-(N-2-methyl)tetrazolyl-2-(1,1-dimethylethoxy)methanamidopropionic acid, methyl ester and 3(N-3-Methyl)tetrazolyl-2-(1,1-dimethylethoxy)methan-amidopropionic acid, methyl ester

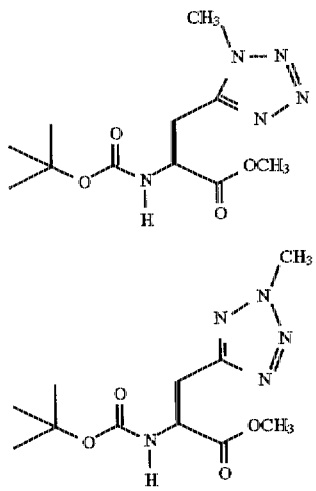

28

1.5 g (5.8 mmol, 1.0 equiv.) of 3-tetrazolyl-2-(1,1-dimethylethoxy) methan-amidopropionic acid 27 was dissolved in 13 mL of dry dimethylformamide and 3.9 g (12.0 mmol, 2.1 equiv.) of cesium carbonate was added. This was followed by the addition of 930 μL (14.5 mmol, 2.5 equiv.) of methyl iodide via syringe. The reaction mixture was stirred at 23° C. for 3 hours and poured into 50 mL of 0.5M hydrochloric acid. The resulting mixture was extracted with ethyl acetate (3×50 mL). The combined organics were washed with 50 mL 0.5M hydrochloric acid, 50 mL saturated sodium bicarbonate, and 50 mL brine. After drying over sodium sulfate, the organics were decanted and the volatiles removed in vacuo on the rotary evaporator to yield a mixture of the title compounds as a yellow oil. The isomers were separated by chromatography on silica gel (50% ethyl acetate/hexane) with one isomer eluting first (Rf=0.3 vs. Rf=0.15 of the other isomer on silica gel developing in 50% ethyl acetate/hexane). Fractions containing pure product were combined and the volatiles removed on the rotovap to yield 0.60 g of pure product for each of the title compounds. $^1$H-NMR (CDCl$_3$): The second-eluting isomer gave 5.8 p.p.m (d, 1H); 4.75 p.p.m (m, 1H); 4.05 p.p.m (s, 3H); 3.75 p.p.m. (s, 3H); 3.4 p.p.m (m, 2H); 1.5 p.p.m. (s, 9H). The first-eluting isomer gave: 5.75 p.p.m (d, 1H); 4.75 p.p.m (m, 1H); 4.30 p.p.m (s, 3H); 3.75 p.p.m. (s, 3H); 3.65 p.p.m (m, 2H); 1.7 p.p.m. (s, 9H).

EXAMPLE 27

Preparation of 3-(N-2-methyl)tetrazolyl-2-(1,1-dimethylethoxy) methanamidopropionic acid or 3-(N-3-methyl) tetrazolyl-2-(1,1-dimethylethoxy) methanamidopropionic

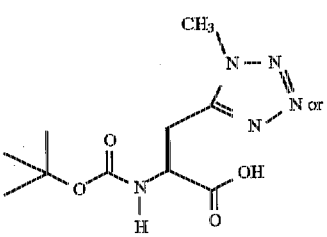

29A

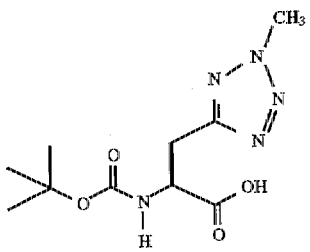

29B 0.5 g (1.75 mmol, 1.0 equiv.) of 3-(N-2-methyl) tetrazolyl-2-(1,1-dimethylethoxy)-methanamidopropionic acid methyl ester or 3-(N-3-methyl) tetrazolyl-2-(1,1-dimethylethoxy)-methanamidopropionic acid methyl ester is dissolved in 12 mL of methanol and 2.3 mL (1.3 equiv.) of 1.0M lithium hydroxide (aq.) is added. The reaction is stirred for 2 hours at 23° C. when starting material can no longer be seen by TLC analysis (1:1 ethyl acetate/hexane). The reaction mixture is passed through a 10 mL bed of Dowex 50X8-400 ion exchange resin and the resin is washed with four column volumes of 1:1 methanol:water. The solvents are removed in vacuo to yield the appropriate title product.

EXAMPLE 28

Preparation of L-3-tetrazolyl-2-(1,1-dimethylethoxy) methanamidopropionyl-L-Pro-L-argininal

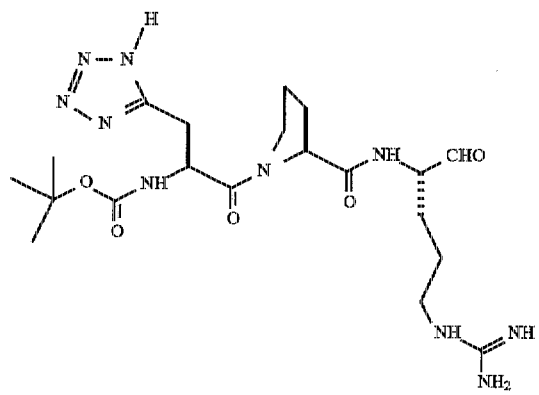

Peptide aldehyde 30 is synthesized and purified in the same manner as described in Example 8. Here, N-BOC-L-proline is first attached to resin 7 followed by 3-tetrazolyl-2-(1,1-dimethylethoxy)methanamidopropionic acid 27 (in the place of N-Boc-L-glutamic acid-γ-benzyl ester). Again, treatment with 50% trifluoroacetic acid is omitted after the last coupling.

EXAMPLE A

Potency—Determination of Inhibitor Constant, $K_i$

The potency of peptide aldehydes, 8, 9, 11 and 12, as inhibitors of bovine and human pancreatic trypsin was quantified in vitro by determination of their inhibitor constants, $K_i$. Enzyme activity was determined using as substrate S-2222 [N-benzoyl-L-isoleucyl-L-glutamyl-glycyl-L-arginine -p-nitroanilide hydrochloride where glutamyl side chain is 50% carboxylic acid and 50% methyl ester], purchased from Kabi Diagnostica. The substrate was made up in deionized water prior to use.

A 96-well microtiter plate was prepared for use in the assay by incubating each well with 300 µL of 1% bovine serum albumin (in deionized water) for 30 minutes at 37° C., and washing three times with deionized water.

To each well was added 50 µL TBS (0.1M Tris, 0.14M NaCl pH 7.4), 50 µL 2.5 nM trypsin and 50 µL peptide aldehyde in TBS or TBS alone. After incubating for 15 minutes at 37° C., 50 µL of S-2222 (at 37° C.) at a specified concentration was added to each well. After mixing, the rate of substrate turnover at 37° C. was measured for 30 minutes at 405 nm (generation of p-nitroaniline). The initial S-2222 concentrations in the assay mixture were 0.45, 0.23, 0.11, 0.056, and 0.028 mM.

$K_i$ was determined graphically using a Dixon plot, as described in Dixon, Biochem. J. 55: 170 (1953). Results are shown in Table 1 below.

TABLE 1

$K_i$ For Peptide Aldehydes Against Trypsin.

| Peptide Aldehyde | Structure | $K_i$ (µM) |
|---|---|---|
| N-t-butoxycarbonyl-L-Glu-L-Pro-L-Argininal | 8 | 0.0014 |
| N-t-butoxycarbonyl-L-Asp-L-Pro-L-Argininal | 9 | 0.00045 |
| N-adamantyloxycarbonyl-L-Asp-L-Pro-L-Argininal | 11 | 0.0002 |
| N-t-butoxycarbonyl-D-Asp-L-Pro-L-Argininal | 12 | 0.045 |

EXAMPLE B

Specificity—Determination of $IC_{50}$

The specificity of the peptide aldehydes (8 through 12) was determined in vitro by measurement of their $IC_{50}$ against other enzymes involved in hemostasis. A specific concentration of enzyme and its substrate were challenged with varying concentrations of inhibitor. $IC_{50}$ is that concentration of inhibitor giving 50% inhibition of substrate turnover, under the assay conditions. Specific assay procedures used are presented below. Tables 2a and 2b below show the results of the specificity assays. ">25" means less than 50% inhibition observed at highest concentration of inhibitor tested, 25 µM inhibitor; "<0.025" means greater than 50% inhibition observed at lowest concentration of inhibitor tested, 0.025 µM; "Inact." means no inhibition observed at highest concentration of inhibitor tested; and "ND" means not determined.

Table 2c and 2d shows % Selectivity relative to trypsin for each compound and commercial inhibitor tested. For each compound, % Selectivity is equal to [$IC_{50}$ for Trypsin)/$IC_{50}$ for other enzyme)] ×100. The lower the numerical value of selectivity, the more selective the compound is as a trypsin inhibitor.

TABLE 2a $IC_{50}$ for Peptide Aldehydes and Commercial Inhibitors.

| Compound Tested | $IC_{50}$ (µM) | | | | |
|---|---|---|---|---|---|
| | Kallikrein | XIa | VIIa | Xa | Thrombin |
| 8 | 6 | 4 | >25 | Inact. | 14 |
| 9 | 17 | 12 | Inact. | >25 | 17 |
| 10 | 8 | 13 | Inact. | 2 | 9 |
| 11 | 2 | 6 | >25 | 0.3 | 10 |
| 12 | >25 | >25 | Inact. | >25 | Inact. |
| Aprotinin | 0.2 | 2 | >25 | Inact. | Inact. |
| Futhan | <0.025 | <0.025 | 1.2 | 6.0 | 0.21 |
| FOY | 1 | 1 | >25 | 8 | 6 |
| Leupeptin | 4 | 11 | >25 | 25 | 20 |

TABLE 2b $IC_{50}$ for Peptide Aldehydes and Commercial Inhibitor.

| Compound Tested | $IC_{50}$ (µM) | | | | |
|---|---|---|---|---|---|
| | Protein C | Plasmin | tPA | UK | Trypsin |
| 8 | Inact. | 0.6 | Inact. | 9 | 0.006 |
| 9 | Inact. | 1.4 | Inact. | 25 | 0.014 |
| 10 | >25 | 1.2 | >25 | >25 | <0.025 |
| 11 | >25 | 1.1 | >25 | 19 | <0.025 |
| 12 | >25 | 1.2 | >25 | 17 | 0.084 |
| Aprotinin | 2 | 0.008 | Inact. | ND | 0.019 |
| Futhan | 0.084 | <0.025 | 0.37 | ND | <0.025 |

TABLE 2b-continued

IC$_{50}$ for Peptide Aldehydes and Commercial Inhibitor.

| Compound Tested | IC$_{50}$ (μM) | | | | |
|---|---|---|---|---|---|
| | Protein C | Plasmin | tPA | UK | Trypsin |
| FOY | 15 | 1.6 | 9 | ND | 0.25 |
| Leupeptin | >25 | 8 | Inact. | Inact. | 1.7 |

TABLE 2c

Calculated % Selectivity for Peptide Aldehydes and Commercial Inhibitors.

| Compound Tested | % Selectivity | | | | |
|---|---|---|---|---|---|
| | Kallikrein | XIa | VIIa | Xa | Thrombin |
| 8 | 0.10 | 0.15 | <0.02 | 0 | 0.04 |
| 9 | 0.08 | 0.12 | 0 | <0.06 | 0.08 |
| 10 | <0.3 | <0.19 | 0 | <1.3 | <0.28 |
| 11 | <1.3 | <0.42 | <0.1 | <0.83 | <0.25 |
| 12 | <0.34 | <0.34 | 0 | <0.34 | 0 |
| Aprotinin | 9.5 | 0.95 | <0.08 | 0 | 0 |
| Futhan | 100 | 100 | <2.1 | <0.42 | <0.12 |
| FOY | 25 | 25 | <1.0 | 3.1 | 4.2 |
| Leupeptin | 43 | 15 | <6.8 | 6.8 | 8.5 |

TABLE 2d

Calculated % Selectivity for Peptide Aldehydes and Commercial Inhibitors

| Compound Tested | % Selectivity | | | | |
|---|---|---|---|---|---|
| | Protein C | Plasmin | tPA | UK | Trypsin |
| 8 | 0 | 1 | 0 | 0.07 | 100 |
| 9 | 0 | 1 | 0 | 0.06 | 100 |
| 10 | <0.1 | <2 | <0.1 | <0.1 | 100 |
| 11 | <0.1 | <2 | <0.1 | <0.1 | 100 |
| 12 | <0.3 | 7 | <0.3 | 0.5 | 100 |
| Aprotinin | 1 | 237 | 0 | — | 100 |
| Futhan | <30 | 100 | <6.8 | — | 100 |
| FOY | 1.7 | 16 | 2.7 | — | 100 |
| Leupeptin | <6.8 | 21 | 0 | 0 | 100 |

(a) Preparation of Microtiter Plates 96-well microtiter plates were prepared for use in these assays by incubating each well with 300 μL 1% bovine serum albumin (in deionized water) for 30 minutes at 37° C., then washing three times with deionized water.

(b) Factor VIIa Assay

Enzyme activity was determined using as substrate, S-2288 [D-isoleucyl-n-prolyl-n-arginine-p-nitroanilide dihydrochloride], purchased from Kabi Diagnostica. The substrate was made up in deionized water prior to use.

Factor VIIa:rTF complex was prepared by adding to a polypropylene test tube 5 mL 25 nM recombinant human tissue factor (rTF), 2.5 ml 400 nM human Factor VIIa (in 0.4% bovine in TBS) and 2.5 mL 20 mM CaCl$_2$. Background control was prepared by adding to a second polypropylene test tube 1 mL 25 nM rTF, 0.5 mL 0.4% bovine serum albumin in TBS, and 0.5 mL 20 mM CaCl$_2$. Both solutions were then incubated for 30 minutes at room temperature before use in the assay.

The assay was run by combining in appropriate wells 50 μL inhibitor in TBS or TBS alone and 100 μL of Factor VIIa:rTF complex or background control, incubating this mixture for 30 minutes at room temperature, adding 50 μL of 2 mM S-2288, incubating for an additional 30 to 60 minutes at room temperature, then reading the absorbance of the wells at 405 nm on a microtiter plate reader set with background substraction at 650 nm.

(c) Factor Xa Assay

Enzyme activity was determined using as substrate, Pefachrome Xa [N-methoxycarbonyl-D-cyclohexylalanyl-L-glycyl-L-arginine p-niroanilide acetate], purchased from Centerchem, Inc. The substrate was made up in deionized water prior to use.

The assay was run by combining in appropriate wells 50 μL of inhibitor in TBS or TBS alone and 50 μL 30 nM human Factor Xa (or TBS as background control) and 50 μL TBS, incubating this mixture for 30 minutes at room temperature, adding 50 μL of 1 mM Pefachrome Xa, incubating for an additional 30 minutes at room temperature, then reading the absorbance of the wells at 405 nm on a microtiter plate reader set with background substraction at 650 nm.

(d) Factor XIa Assay

Enzyme activity was determined using as substrate, S-2366 [L-pyroglutamyl-L-prolyl-L-arginine-p-nitroanilide hydrochloride], purchased from Kabi Diagnostica. The substrate was made up in deionized water prior to use.

The assay was run by combining in appropriate wells 50 μL of inhibitor in TBS or TBS alone and 50 μL of 5 nM human Factor XIa (or TBS as background control) and 50 μL TBS, incubating this mixture for 30 minutes at room temperature, adding 50 μL of 2 mM S-2366, incubating for an additional 30 minutes at room temperature, then reading the absorbance of the wells at 405 nm on a microtiter plate reader set with background substraction at 650 nm.

(e) Thrombin Assay

Enzyme activity was determined using as substrate, S-2238 [D-phenylalanyl-L-pipecolyl-L-arginine-p-nitroanilide dihydrochloride], purchased from Kabi Diagnostica. The substrate was made up in deionized water prior to use.

The assay was run by combining in appropriate wells 50 μL TBS and 50 μL inhibitor in TBS or TBS alone and 50 μL 20 nM bovine thrombin (or TBS as background control), incubating this mixture for 30 minutes at room temperature, adding 50 μL 1 mM S-2238, incubating for an additional 30 minutes at room temperature, then reading the absorbance of the wells at 405 nm on a microtiter plate reader set with background substraction at 650 nm.

(f) Plasmin Assay

Enzyme activity was determined using as substrate, S-2251 [D-valyl-L-leucyl-n-lysine-p-niroanilide dihydrochloride], purchased from Kabi Diagnostica. The substrate was made up in deionized water prior to use.

The assay was run by combining in appropriate wells 50 μL of inhibitor in TBS or TBS alone and 50 μL 25 nM human plasmin (or TBS as background control) and 50 μL TBS, incubating this mixture for 30 minutes at room temperature, adding 50 μL 2 mM S-2251, incubating for an additional 60 to 120 minutes at room temperature, then reading the absorbance of the wells at 405 nmon a microtiter plate reader set with background substraction at 650 nm.

(g) Protein C Assay

Enzyme activity was determined using as substrate, Pefachrome PC [δ-carbobenzoloxy-D-lysyl-n-prolyl-L-arginine-p-nitroanilide], purchased from Centerchem, Inc. The substrate was made up in deionized water prior to use. Protac used to activate Protein C was obtained from American Diagnostics.

Activated human Protein C was prepared by adding to a polypropylene test tube 5 mL of pooled human plasma diluted 1:8 with TBS and 5 mL of 0.117 Units/mL Protac, then incubating for 60 minutes at 37° C.

The assay was run by combining in appropriate wells 50 µL of inhibitor in TBS or TBS alone and 100 µL activated Protein C, incubating this mixture for 30 minutes at room temperature, adding 50 µL 2 mM Pefachrome PC, incubating for an additional 60 minutes at room temperature, then reading the absorbance of the wells at 405 nm on a microtiter plate reader set with background substraction at 650 nm.

(h) Tissue Plasminogen Activator Assay

Enzyme activity was determined using as substrate, S-2288, purchased from Kabi Diagnostica. The substrate was made up in deionized water prior to use.

The assay was run by combining in appropriate wells 50 µL of inhibitor in TBS or TBS alone and 50 µL 50 nM recombinant tissue plasminogen activator (or TBS as background control) and 50 µL TBS, incubating this mixture for 30 minutes at room temperature, adding 50 µL 2 mM S-0 2288, incubating for an additional 60 to 120 minutes at room temperature, then reading the absorbance of the wells at 405 nm on a microtiter plate reader set with background substraction at 650 nm.

(i) Trypsin Assay

Enzyme activity was determined using as substrate S-2222, purchased from Kabi Diagnostica. The substrate was made up in deionized water prior to use.

The assay was run by combining in appropriate wells 50 µL TBS and 50 µL inhibitor in TBS or TBS alone and 50 µL of 40 nM bovine trypsin (or TBS as background control), incubating this mixture for 30 minutes at room temperature, adding 50 µL 1.8 mM S-2222, incubating for an additional 30 minutes at room temperature, then reading the absorbance of the wells at 405 nm on a microtiter plate reader set with background substraction at 650 nm.

(j) Kallikrein Assay

Enzyme activity was determined using as substrate S-2302 [D-prolyl-L-phenylalanyl-L-arginine-p-nitroanilide dihydrochloride], purchased from Kabi Diagnostica. The substrate was made up in deionized water prior to use.

The assay was run by combining in appropriate wells 50 µL TBS and 50 µL of inhibitor in TBS or TBS alone and 50 µL of 4 to 9 nM human kallekrein (or TBS as background control), incubating this mixture for 30 minutes at room temperature, adding 50 µL of 1 mM S-2302, incubating for an additional 30 minutes at room temperature, then reading the absorbance of the wells at 405 nm on a microtiter plate reader set with background substraction at 650 nm.

(k) Urokinase Assay.

Enzyme activity was determined using as substrate S-2444 [L-pyroglutamyl-L-glycyl-n-arginine-p-nitroanilide hydrochloride], purchased from Kabi Diagnostica. The substrate was made up in deionized water prior to use.

The assay was run by combining in appropriate wells 50 µL inhibitor in TBS or TBS alone and 50 µL of 270 U/mL human urokinase (or TBS as background control) and 50 µL TBS, incubating this mixture for 30 minutes at room temperature, adding 50 µL 1 mM S-2444, incubating for an additional 30 minutes at room temperature, then reading the absorbance of the wells at 405 nm on a microtiter plate reader set with background substraction at 650 nm.

EXAMPLE C

Animal Model for Pancreatitis

Niederau et al., Gastroenterology, 88: 1192–1204 (1985) showed that acute necrotizing pancreatitis can be induced in mice by intraperitoneal (IP) injections of caerulein. When so induced, serum amylase levels were found to rise and fall with the severity and course of inflammatory process.

Pancreatitis was induced in fasting male balb/c mice weighing between 18 to 20 g by giving them three IP injections of caerulein, with each dose at 100 µg/kg body weight. The injections of each were given at two hour intervals over a 6 hour period. The ability of N-Boc-L-Asp-Pro-Arg-al (compound 9) to inhibit the induced pancreatitis was tested by injection into caerulein-treated mice. The inhibitor was dissolved into TBS, then injected IP into the mice. The first injection was given 1/4 hour prior to the caerulein treatment, then one hour after each caerulein injection. Inhibitor dose tested was 50 mg/kg body weight.

A blood serum sample was drawn and tested for amylase concentration. The blood sample was obtained by periorbital bleeding into heparized tubes 4 hours after the last injection of inhibitor. After centrifuging to remove the blood cells, the serum was the diluted 1:10 in TBS and assayed with Sigma Diagnostics Amylase reagent. The kinetic change in absorbance was measured at 405nm for 1 minute, then was converted into U/ml amylase activity.

TABLE 3

| (Amylase Activity (U/ml) | | |
|---|---|---|
| | Mean ± S.D | n |
| Saline + caerulein | 64.4 ± 14.4[a] | 7 |
| N-Boc-L-Asp-Pro-Arg-al + caerulein | 40.8 ± 5.2[a,b] | 8 |
| Control (no caerulein) | 10.4 ± 1.6 | 5 |

[a]—p < 0.01 vs control by Newman-Keuls test
[b]—p < 0.01 vs saline + caerulein by Newman-Keuls test These data show the protective effect of inhibitors of this invention in vivo.

Having described the invention, it will be apparent to one of ordinary skill in the art that changes and modifications can be made without departing from the spirit and scope of the invention as set forth herein. Other embodiments are within the following claims.

We claim:

1. Method for synthesis of a peptide aldehyde, comprising the steps of:

reacting a semicarbazide having the formula:

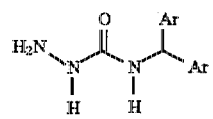

wherein Ar is phenyl or an equivalent thereof,
with an α-N-protected amino aldehyde to produce a protected semi-carbazone,
deprotecting the α-amino group of said protected semi-carbazone, and
reacting the deprotected semi-carbazone with an N-protected amino acid to produce an N-protected peptide aldehyde.

2. The method of claim 1, wherein said Ar is phenyl.

3. The method of claim 1 wherein said amino aldehyde is argininal.

4. The method of claim 1 wherein said deprotecting and reacting the deprotected semi-carbazone steps are repeated a plurality of times with either the same said N-protected amino acid or a different N-protected amino acid.

5. The method of claim 1 wherein said Ar has the formula:

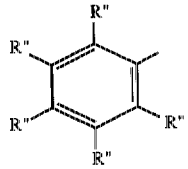

wherein each R" is selected independently from the group consisting of H, methyl, methoxy, halogen, ethyl and ethoxy.

6. Protected semi-carbazone formed by reacting a semicarbazide, having the formula:

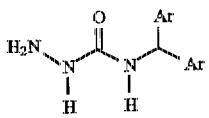

wherein Ar is phenyl or an equivalent thereof, with an α-N-protected amino aldehyde to produce said protected semi-carbazone wherein the aldehyde group of said α-N-protected amino aldehyde reacts at the NH group of said semicarbazide and thereby links said amino aldehyde to said semicarbazide by replacing the hydrogens of said $NH_2$ group of said semicarbazide.

* * * * *